(12) United States Patent
Vassiliades et al.

(10) Patent No.: US 11,027,103 B2
(45) Date of Patent: *Jun. 8, 2021

(54) CONDUIT DEVICE AND SYSTEM FOR IMPLANTING A CONDUIT DEVICE IN A TISSUE WALL

(71) Applicants: EMORY UNIVERSITY, Atlanta, GA (US); GEORGIA TECH RESEARCH CORPORATION, Atlanta, GA (US)

(72) Inventors: Thomas A. Vassiliades, Atlanta, GA (US); Ajit Yoganathan, Tucker, GA (US); Jorge Heman Jimenez, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 511 days.

This patent is subject to a terminal disclaimer.

(21) Appl. No.: 15/919,975

(22) Filed: Mar. 13, 2018

(65) Prior Publication Data
US 2018/0200492 A1    Jul. 19, 2018

Related U.S. Application Data

(63) Continuation of application No. 15/058,703, filed on Mar. 2, 2016, now Pat. No. 9,950,146, which is a
(Continued)

(51) Int. Cl.
*A61M 27/00* (2006.01)
*A61B 17/3205* (2006.01)
(Continued)

(52) U.S. Cl.
CPC ..... *A61M 27/002* (2013.01); *A61B 17/32053* (2013.01); *A61F 2/064* (2013.01);
(Continued)

(58) Field of Classification Search
CPC .......... A61M 27/002; A61M 2210/125; A61M 1/1008; A61M 1/122; A61M 1/10;
(Continued)

(56) References Cited

U.S. PATENT DOCUMENTS 3,512,519 A    5/1970   Hall
3,540,451 A   11/1970   Zeman
(Continued)

FOREIGN PATENT DOCUMENTS

CA    2 526 920    2/2009
CN     1842354    10/2006
(Continued)

OTHER PUBLICATIONS

International Search Report and Written Opinion for International Patent Application No. PCT/US2008/061404, dated Aug. 19, 2008.
(Continued)

*Primary Examiner* — Adam Marcetich
(74) *Attorney, Agent, or Firm* — Womble Bond Dickinson (US) LLP

(57) ABSTRACT

Various embodiments of the present invention provide a conduit device including an attaching device configured for defining a helical pathway through a tissue wall and complementary ring in cooperation for securing the device within an aperture defined in the tissue wall. Some embodiments of the present invention further provide a system for implanting a conduit device in a tissue wall. More specifically, some embodiments provide a system including a coring device for defining an aperture in a tissue by removing and retaining a tissue core and securely implanting a conduit device therein so as to provide fluid communication between a first and second surface of the tissue wall via the conduit device.

20 Claims, 8 Drawing Sheets

Related U.S. Application Data continuation of application No. 14/475,068, filed on Sep. 2, 2014, now Pat. No. 9,308,015, which is a continuation of application No. 13/845,960, filed on Mar. 18, 2013, now Pat. No. 8,858,489, which is a continuation of application No. 12/901,810, filed on Oct. 11, 2010, now Pat. No. 8,430,836, which is a continuation of application No. 11/739,151, filed on Apr. 24, 2007, now Pat. No. 7,846,123.

(51) Int. Cl.

| | | |
|---|---|---|
| *A61F 2/06* | (2013.01) | |
| *A61B 17/00* | (2006.01) | |
| *A61B 17/34* | (2006.01) | |
| *A61M 60/00* | (2021.01) | |
| *A61M 60/122* | (2021.01) | |
| *A61M 60/148* | (2021.01) | |
| *A61M 60/857* | (2021.01) | |
| *A61B 17/11* | (2006.01) | |
| *A61B 18/00* | (2006.01) | |

(52) U.S. Cl.
CPC ..... *A61B 17/11* (2013.01); *A61B 2017/00123* (2013.01); *A61B 2017/00243* (2013.01); *A61B 2017/00252* (2013.01); *A61B 2017/3488* (2013.01); *A61B 2018/00351* (2013.01); *A61B 2018/00392* (2013.01); *A61M 60/00* (2021.01); *A61M 60/122* (2021.01); *A61M 60/148* (2021.01); *A61M 60/857* (2021.01); *A61M 2210/1085* (2013.01); *A61M 2210/125* (2013.01); *Y10S 623/904* (2013.01)

(58) Field of Classification Search
CPC .... A61M 1/12; A61B 17/32053; A61B 17/11; A61B 2017/00243; A61B 2018/00351; A61B 2017/00252; A61B 2017/3488; A61F 2/064; Y10S 623/904
See application file for complete search history.

(56) References Cited

U.S. PATENT DOCUMENTS

| | | | |
|---|---|---|---|
| 3,856,021 A | 12/1974 | McIntosh | |
| 4,204,541 A | 5/1980 | Kapitanov | |
| 4,366,819 A | 1/1983 | Kaster | |
| 4,769,031 A | 9/1988 | McGough et al. | |
| 4,904,264 A | 2/1990 | Scheunemann | |
| 4,955,856 A | 9/1990 | Phillips | |
| 5,098,369 A | 3/1992 | Heilman et al. | |
| 5,129,913 A | 7/1992 | Ruppert | |
| 5,139,517 A | 8/1992 | Corral | |
| 5,158,563 A | 10/1992 | Cosman | |
| 5,222,980 A | 6/1993 | Gealow | |
| 5,256,160 A | 10/1993 | Clement | |
| 5,290,639 A | 3/1994 | Mallory | |
| 5,291,179 A | 3/1994 | Ooe et al. | |
| 5,387,193 A | 2/1995 | Miraki | |
| 5,447,533 A | 9/1995 | Vachon et al. | |
| 5,456,714 A | 10/1995 | Owen | |
| 5,488,958 A * | 2/1996 | Topel ............. | A61B 17/320016 600/567 |
| 5,562,729 A | 10/1996 | Purdy et al. | |
| 5,577,993 A | 11/1996 | Zhu et al. | |
| 5,582,616 A | 12/1996 | Bolduc et al. | |
| 5,695,504 A | 12/1997 | Gifford et al. | |
| 5,728,116 A | 3/1998 | Rosenman | |
| 5,738,680 A | 4/1998 | Mueller et al. | |
| 5,755,697 A | 5/1998 | Jones et al. | |
| 5,782,844 A | 7/1998 | Yoon et al. | |
| 5,797,933 A | 8/1998 | Snow et al. | |
| 5,810,836 A | 9/1998 | Hussein et al. | |
| 5,810,851 A | 9/1998 | Yoon | |
| 5,814,005 A | 9/1998 | Barra et al. | |
| 5,824,070 A | 10/1998 | Jarvik | |
| 5,824,071 A | 10/1998 | Nelson et al. | |
| 5,827,316 A | 10/1998 | Young et al. | |
| 5,833,698 A | 11/1998 | Hinchliffe et al. | |
| 5,843,088 A | 12/1998 | Barra et al. | |
| 5,865,791 A | 2/1999 | Whayne et al. | |
| 5,893,369 A | 4/1999 | LeMole | |
| 5,910,153 A | 6/1999 | Mayengerger | |
| 5,924,424 A | 7/1999 | Stevens et al. | |
| 5,944,730 A | 8/1999 | Nobles et al. | |
| 5,976,174 A | 11/1999 | Ruiz | |
| 5,984,956 A | 11/1999 | Tweden et al. | |
| 5,989,278 A | 11/1999 | Mueller | |
| 6,001,056 A | 12/1999 | Jassawalla et al. | |
| 6,007,576 A | 12/1999 | McClellan | |
| 6,022,324 A | 2/2000 | Skinner | |
| 6,022,367 A | 2/2000 | Sherts | |
| 6,024,755 A | 2/2000 | Addis | |
| 6,039,748 A | 3/2000 | Savage et al. | |
| 6,066,085 A | 5/2000 | Heilman et al. | |
| 6,079,414 A | 6/2000 | Roth | |
| 6,080,173 A | 6/2000 | Williamson et al. | |
| 6,080,176 A | 6/2000 | Young | |
| 6,113,611 A | 9/2000 | Allen et al. | |
| 6,146,325 A | 11/2000 | Lewis et al. | |
| 6,241,743 B1 | 6/2001 | Levin et al. | |
| 6,254,564 B1 | 7/2001 | Wilk et al. | |
| 6,267,732 B1 | 7/2001 | Heneveld et al. | |
| 6,273,862 B1 | 8/2001 | Privitera et al. | |
| 6,290,728 B1 | 9/2001 | Phelps et al. | |
| 6,346,071 B1 | 2/2002 | Mussivand | |
| 6,390,976 B1 | 5/2002 | Spence et al. | |
| 6,401,720 B1 | 6/2002 | Stevens et al. | |
| 6,409,739 B1 | 6/2002 | Nobles et al. | |
| 6,443,957 B1 | 9/2002 | Addis | |
| 6,458,140 B2 | 10/2002 | Akin et al. | |
| 6,506,197 B1 | 1/2003 | Rollero et al. | |
| 6,537,300 B2 | 3/2003 | Girton | |
| 6,551,319 B2 | 4/2003 | Lieberman | |
| 6,551,322 B1 | 4/2003 | Lieberman | |
| 6,551,332 B1 | 4/2003 | Nguyen et al. | |
| 6,582,400 B1 * | 6/2003 | Hawk ................ | A61B 17/3478 604/164.01 |
| 6,589,277 B1 | 7/2003 | Fabiani et al. | |
| 6,607,541 B1 | 8/2003 | Gardiner et al. | |
| 6,638,237 B1 | 10/2003 | Guiles et al. | |
| 6,651,670 B2 | 11/2003 | Rapacki et al. | |
| 6,663,633 B1 | 12/2003 | Pierson, III | |
| 6,669,708 B1 | 12/2003 | Nissenbaum et al. | |
| 6,673,043 B1 | 1/2004 | Landesberg | |
| 6,676,678 B2 | 1/2004 | Gifford et al. | |
| 6,689,147 B1 | 2/2004 | Koster, Jr. | |
| 6,695,859 B1 | 2/2004 | Golden et al. | |
| 6,699,256 B1 | 3/2004 | Logan et al. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,740,101 B2 | 5/2004 | Houser et al. | |
| 6,776,787 B2 | 8/2004 | Phung et al. | |
| 6,802,806 B2 | 10/2004 | McCarthy et al. | |
| 6,808,498 B2 | 10/2004 | Laroya et al. | |
| 6,824,071 B1 | 11/2004 | McMichael | |
| 6,827,683 B2 | 12/2004 | Otawara | |
| 6,863,677 B2 | 3/2005 | Breznock | |
| 6,869,437 B1 | 3/2005 | Hausen et al. | |
| 6,942,672 B2 | 9/2005 | Heilman et al. | |
| 6,978,176 B2 | 12/2005 | Lattouf | |
| 6,984,241 B2 | 1/2006 | Lubbers et al. | |
| 6,994,666 B2 | 2/2006 | Shannon et al. | |
| 7,018,384 B2 | 3/2006 | Skakoon | |
| 7,033,372 B1 | 4/2006 | Cahalan | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,083,631 B2 | 8/2006 | Houser et al. | |
| 7,163,525 B2 | 1/2007 | Franer | |
| 7,182,771 B1 | 2/2007 | Houser et al. | |

(56) References Cited

U.S. PATENT DOCUMENTS

| | | |
|---|---|---|
| 7,214,234 B2 | 5/2007 | Rapacki et al. |
| 7,232,421 B1 | 6/2007 | Gambale et al. |
| 7,258,694 B1 | 8/2007 | Choi et al. |
| 7,309,343 B2 | 12/2007 | Vargas et al. |
| 7,331,956 B2 | 2/2008 | Hovda et al. |
| 7,404,792 B2 | 7/2008 | Spence et al. |
| 7,510,561 B2 | 3/2009 | Beane et al. |
| 7,637,919 B2 | 12/2009 | Ishikawa et al. |
| 7,717,844 B2 | 5/2010 | Cohn |
| 7,744,527 B2 | 6/2010 | Cohn |
| 7,766,811 B2 | 8/2010 | Haverich |
| 7,799,041 B2 | 9/2010 | Beane et al. |
| 7,842,068 B2 | 11/2010 | Ginn |
| 7,846,123 B2 | 12/2010 | Vassiliades et al. |
| 7,846,179 B2 | 12/2010 | Belef et al. |
| 7,931,581 B2 | 4/2011 | Cohn |
| 7,942,805 B2 | 5/2011 | Shambaugh, Jr. |
| 7,993,392 B2 | 8/2011 | Righini et al. |
| 8,226,670 B2 | 7/2012 | Beane et al. |
| 8,430,836 B2 | 4/2013 | Vassiliades et al. |
| 8,556,930 B2 | 10/2013 | Ellingwood |
| 8,579,790 B2 | 11/2013 | Jeffery et al. |
| 8,764,795 B2 | 7/2014 | Whitman et al. |
| 8,840,538 B2 | 9/2014 | Jeffery et al. |
| 8,858,489 B2 | 10/2014 | Vassiliades et al. |
| 2001/0051809 A1 | 12/2001 | Houser et al. |
| 2002/0019623 A1 | 2/2002 | Altman et al. |
| 2002/0019643 A1 | 2/2002 | Gifford et al. |
| 2002/0032462 A1 | 3/2002 | Houser et al. |
| 2002/0038127 A1 | 3/2002 | Blatter et al. |
| 2002/0045846 A1 | 4/2002 | Kaplon et al. |
| 2002/0055737 A1 | 5/2002 | Lieberman |
| 2002/0055738 A1 | 5/2002 | Lieberman |
| 2002/0055739 A1 | 5/2002 | Lieberman |
| 2002/0055740 A1 | 5/2002 | Lieberman |
| 2002/0055742 A1 | 5/2002 | Lieberman |
| 2002/0058958 A1 | 5/2002 | Walen |
| 2002/0095210 A1 | 7/2002 | Finnegan et al. |
| 2002/0099394 A1 | 7/2002 | Houser et al. |
| 2002/0116018 A1 | 8/2002 | Stevens et al. |
| 2002/0177865 A1 | 11/2002 | McIntosh |
| 2002/0183786 A1 | 12/2002 | Girton |
| 2002/0193806 A1 | 12/2002 | Moenning et al. |
| 2003/0014064 A1 | 1/2003 | Blatter |
| 2003/0023255 A1 | 1/2003 | Miles et al. |
| 2003/0032979 A1 | 2/2003 | Mortier et al. |
| 2003/0040765 A1 | 2/2003 | Breznock |
| 2003/0045834 A1 | 3/2003 | Wing et al. |
| 2003/0078592 A1 | 4/2003 | Heilman et al. |
| 2003/0078597 A1* | 4/2003 | Blatter ............... A61B 17/0644 606/139 |
| 2003/0130668 A1 | 7/2003 | Nieman et al. |
| 2003/0181843 A1 | 9/2003 | Bibber et al. |
| 2003/0181913 A1 | 9/2003 | Lieberman |
| 2004/0002624 A1 | 1/2004 | Yu et al. |
| 2004/0050393 A1 | 3/2004 | Golden et al. |
| 2004/0068299 A1 | 4/2004 | Laske et al. |
| 2004/0073216 A1 | 4/2004 | Lieberman |
| 2004/0077989 A1 | 4/2004 | Goode et al. |
| 2004/0092858 A1 | 5/2004 | Wilson et al. |
| 2004/0097973 A1 | 5/2004 | Loshakove et al. |
| 2004/0097993 A1 | 5/2004 | Whayne |
| 2004/0098011 A1 | 5/2004 | Vargas et al. |
| 2004/0133155 A1 | 7/2004 | Varner et al. |
| 2004/0138701 A1 | 7/2004 | Peartree et al. |
| 2004/0153112 A1 | 8/2004 | Nissenbaum et al. |
| 2004/0158308 A1 | 8/2004 | Hogendijk et al. |
| 2004/0162608 A1 | 8/2004 | Haverich |
| 2004/0167547 A1 | 8/2004 | Beane et al. |
| 2004/0167551 A1 | 8/2004 | Gifford, III et al. |
| 2004/0171905 A1 | 9/2004 | Yu et al. |
| 2004/0186490 A1 | 9/2004 | Gifford et al. |
| 2004/0225306 A1 | 11/2004 | Blatter et al. |
| 2004/0236170 A1 | 11/2004 | Kim |
| 2005/0033107 A1 | 2/2005 | Tsubouchi |
| 2005/0043781 A1 | 2/2005 | Foley |
| 2005/0075656 A1 | 4/2005 | Beaupre |
| 2005/0085883 A1* | 4/2005 | Ollivier ............. A61M 25/0084 607/116 |
| 2005/0101982 A1 | 5/2005 | Ravenscroft et al. |
| 2005/0101983 A1 | 5/2005 | Loshakove et al. |
| 2005/0131451 A1 | 6/2005 | Kleshinski et al. |
| 2005/0137609 A1 | 6/2005 | Guiraudon |
| 2005/0149093 A1 | 7/2005 | Pokorney |
| 2005/0154411 A1 | 7/2005 | Breznock et al. |
| 2005/0171479 A1 | 8/2005 | Hruska et al. |
| 2005/0177180 A1* | 8/2005 | Kaganov ............... A61F 2/2445 606/151 |
| 2005/0187568 A1 | 8/2005 | Klenk et al. |
| 2005/0192604 A1 | 9/2005 | Carson et al. |
| 2005/0209502 A1 | 9/2005 | Schmid et al. |
| 2005/0222582 A1 | 10/2005 | Wenchell |
| 2005/0250987 A1* | 11/2005 | Ewers ................. A61B 17/0401 600/102 |
| 2005/0251187 A1 | 11/2005 | Beane et al. |
| 2005/0256368 A1 | 11/2005 | Klenk et al. |
| 2005/0267495 A1 | 12/2005 | Ginn et al. |
| 2006/0020326 A9 | 1/2006 | Bolduc et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2006/0167333 A1 | 7/2006 | Moore et al. |
| 2006/0178675 A1 | 8/2006 | Hamman |
| 2006/0241659 A1 | 10/2006 | Tulleken et al. |
| 2006/0259050 A1 | 11/2006 | De Winter |
| 2007/0010834 A1 | 1/2007 | Sharkawy et al. |
| 2007/0055357 A1 | 3/2007 | Pokorney et al. |
| 2007/0060952 A1 | 3/2007 | Roby et al. |
| 2007/0066943 A1 | 3/2007 | Prasad et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0106328 A1 | 5/2007 | Wardle et al. |
| 2007/0112361 A1 | 5/2007 | Schonholz et al. |
| 2007/0142849 A1* | 6/2007 | Ewers .................... A61B 17/30 606/153 |
| 2007/0167968 A1 | 7/2007 | Pandey |
| 2007/0167969 A1 | 7/2007 | Pandey |
| 2007/0173879 A1 | 7/2007 | Pandey |
| 2007/0197856 A1 | 8/2007 | Gellman et al. |
| 2007/0208214 A1 | 9/2007 | Hjelle et al. |
| 2007/0265643 A1 | 11/2007 | Beane et al. |
| 2008/0004640 A1 | 1/2008 | Ellingwood |
| 2008/0009668 A1 | 1/2008 | Cohn |
| 2008/0009887 A1 | 1/2008 | Cohn |
| 2008/0009891 A1 | 1/2008 | Cohn |
| 2008/0039883 A1 | 2/2008 | Nohilly |
| 2008/0058846 A1 | 3/2008 | Vosough |
| 2008/0076959 A1 | 3/2008 | Farnan et al. |
| 2008/0161826 A1 | 7/2008 | Guiraudon |
| 2008/0177301 A1 | 7/2008 | Svensson |
| 2008/0255597 A1 | 10/2008 | Pravong et al. |
| 2009/0012552 A1 | 1/2009 | Pandey et al. |
| 2009/0012557 A1* | 1/2009 | Osypka ............... A61B 17/0482 606/213 |
| 2009/0082778 A1 | 3/2009 | Beane et al. |
| 2009/0112062 A1 | 4/2009 | Bakos |
| 2009/0203957 A1 | 8/2009 | LaRose et al. |
| 2009/0204206 A1 | 8/2009 | Parquet et al. |
| 2009/0240264 A1 | 9/2009 | Tuval et al. |
| 2010/0004739 A1 | 1/2010 | Vesely |
| 2010/0010500 A1 | 1/2010 | Beane et al. |
| 2010/0010616 A1 | 1/2010 | Drews et al. |
| 2010/0049225 A1 | 2/2010 | To et al. |
| 2010/0087907 A1 | 4/2010 | Lattouf |
| 2010/0160847 A1 | 6/2010 | Braido et al. |
| 2010/0161040 A1 | 6/2010 | Braido et al. |
| 2010/0168778 A1 | 7/2010 | Braido |
| 2011/0092766 A1 | 4/2011 | Almog et al. |
| 2011/0106116 A1 | 5/2011 | Ducharme et al. |
| 2011/0118766 A1 | 5/2011 | Reichenbach et al. |

(56) References Cited

U.S. PATENT DOCUMENTS

| | | |
|---|---|---|
| 2011/0118770 A1 | 5/2011 | Pokorney et al. |
| 2011/0118833 A1 | 5/2011 | Reichenbach et al. |
| 2011/0144680 A1 | 6/2011 | Nguyen et al. |
| 2011/0160850 A1 | 6/2011 | Bourque |
| 2011/0190811 A1 | 8/2011 | Shanley |
| 2011/0196190 A1 | 8/2011 | Farnan et al. |
| 2011/0224785 A1 | 9/2011 | Hacohen |
| 2011/0251450 A1 | 10/2011 | Pagani et al. |
| 2012/0059212 A1 | 3/2012 | LaRose et al. |
| 2012/0059457 A1 | 3/2012 | Leinsing et al. |
| 2012/0089181 A1 | 4/2012 | Shanley et al. |
| 2012/0123452 A1 | 5/2012 | Asfora et al. |
| 2012/0123461 A1 | 5/2012 | Gillies et al. |
| 2012/0226096 A1 | 9/2012 | Callaway et al. |
| 2012/0253386 A1 | 10/2012 | Rowe et al. |
| 2012/0296151 A1 | 11/2012 | Curtis et al. |
| 2012/0296358 A1 | 11/2012 | Nguyen et al. |
| 2013/0012761 A1 | 1/2013 | Gregoric et al. |
| 2013/0110228 A1 | 5/2013 | Braido |
| 2013/0116728 A1 | 5/2013 | Litvack et al. |
| 2013/0150654 A1 | 6/2013 | Stanfield et al. |
| 2013/0218169 A1 | 8/2013 | Vassiliades et al. |
| 2013/0253641 A1 | 9/2013 | Lattouf |
| 2014/0039375 A1 | 2/2014 | Jimenez et al. |
| 2014/0067057 A1 | 3/2014 | Callaway et al. |
| 2014/0100430 A1 | 4/2014 | Beane et al. |
| 2014/0148786 A1 | 5/2014 | Milo |
| 2014/0194833 A1 | 7/2014 | Andrus |
| 2014/0214159 A1 | 7/2014 | Vidlund et al. |
| 2014/0378772 A1 | 12/2014 | Sundt, III et al. |
| 2014/0379074 A1 | 12/2014 | Spence et al. |
| 2015/0032153 A1 | 1/2015 | Quadri et al. |
| 2015/0038770 A1 | 2/2015 | Colella |
| 2015/0112120 A1 | 4/2015 | Andrus |
| 2015/0196321 A1 | 7/2015 | Gregory et al. |
| 2015/0359952 A1 | 12/2015 | Andrus et al. |
| 2016/0095705 A1 | 4/2016 | Keranen et al. |

FOREIGN PATENT DOCUMENTS

| | | |
|---|---|---|
| EP | 1 669 042 | 6/2006 |
| EP | 1 691 884 | 3/2011 |
| EP | 1 628 702 | 5/2013 |
| EP | 1 706 168 | 11/2013 |
| JP | HI 1-500642 | 1/1999 |
| JP | 2002-518082 | 6/2002 |
| JP | 2006-514569 | 5/2006 |
| JP | 2006-518624 | 8/2006 |
| JP | 2007-510522 | 4/2007 |
| WO | WO 93/25148 | 12/1993 |
| WO | WO 96/25886 | 8/1996 |
| WO | WO 97/13463 | 4/1997 |
| WO | WO 99/65409 | 12/1999 |
| WO | WO 00/00193 | 1/2000 |
| WO | WO 00/15147 | 3/2000 |
| WO | WO 00/15149 | 3/2000 |
| WO | WO 00/41759 | 7/2000 |
| WO | WO 00/74747 | 12/2000 |
| WO | WO 03/001980 | 1/2003 |
| WO | WO 2004/026147 | 4/2004 |
| WO | WO 2004/096059 | 11/2004 |
| WO | WO 2004/096337 | 11/2004 |
| WO | WO 2005/046783 | 5/2005 |
| WO | WO 2006/019755 | 2/2006 |
| WO | WO 2006/020651 | 2/2006 |
| WO | WO 2006/093970 | 9/2006 |
| WO | 2007/047933 | 4/2007 |
| WO | WO 2007/038109 | 4/2007 |
| WO | WO 2007/047212 | 4/2007 |
| WO | WO 2007/117612 | 10/2007 |
| WO | WO 2008/131453 | 10/2008 |
| WO | WO 2008/153872 | 12/2008 |
| WO | WO 2009/100198 | 8/2009 |
| WO | WO 2009/117435 | 9/2009 |
| WO | 2012/025927 | 3/2012 |
| WO | WO 2012/040233 | 3/2012 |
| WO | WO-2012106422 | 8/2012 |
| WO | WO 2013/064529 | 5/2013 |
| WO | 2013/189620 | 12/2013 |
| WO | 2015/109328 | 7/2015 |

OTHER PUBLICATIONS

International Preliminary Report on Patentability for International Patent Application No. PCT/US2008/061404, dated Oct. 27, 2009.
Office Action for European Patent Application No. 08 799 829.0, dated Apr. 19, 2012.
Office Action for European Patent Application No. 08 799 829.0, dated Nov. 2, 2012.
Office Action for Japanese Patent Application No. 2010-606491, dated Nov. 13, 2012.
Office Action for European Patent Application No. 08 799 829.0, dated May 27, 2013.
Office Action for Japanese Patent Application No. 2010-606491, dated Jul. 5, 2013.
Extended European Search Report for European Patent Application No. 13 186 508.1, dated Feb. 6, 2014.
Office Action or European Patent Application No. 13 186 508.1, dated Mar. 17, 2014.
Office Action for Canadian Patent Application No. 2,719,951, dated Apr. 30, 2014.
English Translation of Office Action for Japanese Patent Application No. 2013-175430, dated Jul. 11, 2014.
Notice of Allowance for Canadian Patent Application No. 2,719,951, dated Feb. 5, 2015.
English Translation of Office Action for Japanese Patent Application No. 2013-175430, dated May 19, 2015.
Office Action for Japanese Patent Application No. 2013-175430, dated Jan. 5, 2016.

\* cited by examiner

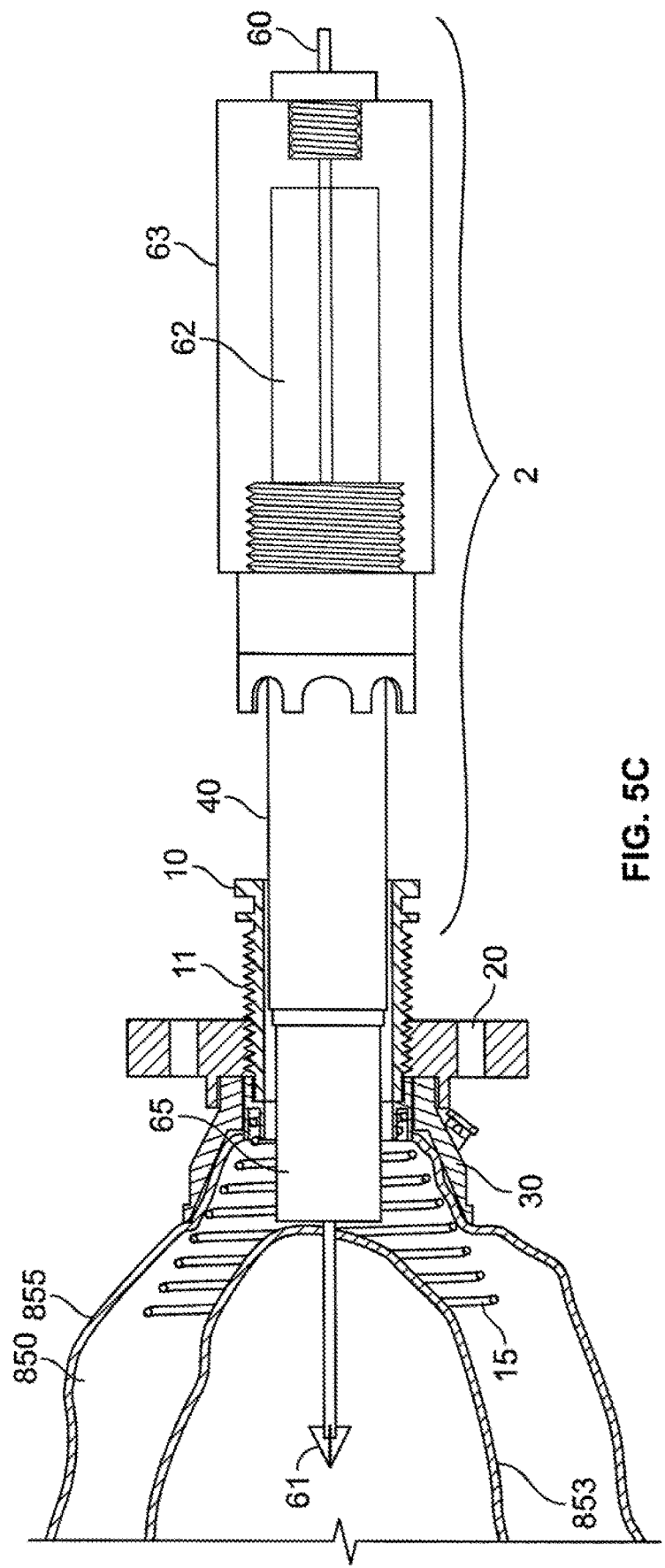

CONDUIT DEVICE AND SYSTEM FOR IMPLANTING A CONDUIT DEVICE IN A TISSUE WALL

CROSS-REFERENCE TO RELATED APPLICATIONS

The present application is a continuation of co-pending U.S. patent application Ser. No. 15/058,703, filed on Mar. 2, 2016, which is a continuation of U.S. patent application Ser. No. 14/475,068, now U.S. Pat. No. 9,308,015, which is a continuation of U.S. patent application Ser. No. 13/845,960, filed on Mar. 18, 2013, now U.S. Pat. No. 8,858,489, which is a continuation of U.S. patent application No. Ser. No. 12/901,810, filed on Oct. 11, 2010, now U.S. Pat. No. 8,430,836 issued on Apr. 30, 2013, which is a continuation of U.S. patent application Ser. No. 11/739,151, filed on Apr. 24, 2007, now U.S. Pat. No. 7,846,123 issued on Dec. 7, 2010, which are hereby incorporated by reference in their entireties herein.

FIELD OF INVENTION

This invention relates to devices and methods for creating and maintaining a fluid conduit to establish fluid communication between opposing surfaces of a tissue wall.

BACKGROUND OF THE INVENTION

Construction of an alternative conduit between the left ventricle and the aorta (an apicoaortic conduit, or AAC) to create a double-outlet left ventricle (LV) has been successfully employed to treat a variety of complex congenital LV outflow obstruction (fibrous tunnel obstruction, aortic annular hypoplasia, tubular hypoplasia of the ascending aorta, and patients with diffuse septal thickening, severe LV hypertrophy and a small LV cavity) as well as adult-onset aortic stenosis in patients with complicating preoperative conditions (previous failed annular augmentation procedures, previous infection, previous CABG with patent anterior internal mammary artery grafts, and a porcelain ascending aorta).

However, the AAC insertion procedure has been poorly accepted, primarily because of early valve failures using first-generation bioprostheses as well as the success of direct LVOTO repair and aortic valve replacement. In the United States, despite an aging population, the unadjusted mortality for isolated aortic valve operations in 2001 remained under 4%. Further, the AAC insertion operation, with or without cardiopulmonary bypass, has not been as technically straightforward as direct aortic valve replacement. For most surgeons, AAC insertion is not a familiar operation and is of historical interest only.

Nonetheless, several studies have demonstrated that AAC insertion successfully lessens the LV-aortic pressure gradient, preserves or improves ventricular function and maintains normally distributed blood flow through the systemic and coronary circulation. While there have been several techniques described, the most commonly employed method is the lateral thoracotomy approach with placement of the AAC to the descending aorta. Other techniques include a median sternotomy approach with insertion of the distal limb of the AAC to the ascending aorta, to the transverse part of the aortic arch, or to the intra-abdominal supraceliac aorta.

In general, the thoracic aorta and the left ventricle apex are exposed through a left lateral thoracotomy, and a needle is passed through the apex and into the left ventricle. While the connector is still spaced apart from the apex, the sutures that will fix the connector to the apex are threaded through a cuff on the connector and through the apex in a matching pattern. The cuff is set back from the end of the connector by 1-2 centimeters to allow the end of the connector to extend through the heart muscle and into the left ventricle. Once the sutures are in place, a ventricular coring device is used to remove a core of ventricular muscle, and the pre-threaded sutures are then pulled to draw the connector into the opening until the cuff comes to rest on the apex. The sutures are tied off, and additional sutures may be added. Either before or after this procedure, the opposite end of the connector is attached to a valved conduit which terminates at the aorta.

The current techniques and technology available to perform AAC insertion were originally designed to be performed on-pump; either with an arrested or fibrillating heart. While off-pump cases have been described, they can be technically difficult due to the shortcomings of presently available conduits and systems for installing such conduits. For example, because existing conduits require the use of sutures to reliably secure the connector in place, it is often difficult for surgeons or other clinicians to insert such sutures reliably in active cardiac and/or vascular tissue.

Some devices and methods have been devised to install an AAC conduit, such as those described generally in U.S. patent application Ser. No. 11/251,100, filed on Oct. 14, 2005, and U.S. patent application Ser. No. 10/915,691, filed on Aug. 11, 2004, both of which are hereby incorporated herein in their entirety by reference. However, these AAC conduit devices and installation systems rely on the use of a flexible flange that is inserted through a pre-defined aperture in the ventricular apex. Thus, such methods require the use of a hemostatic device (such as an occlusion balloon and/or "umbrella" device) to prevent blood loss from the aperture during installation of the AAC conduit.

SUMMARY OF THE INVENTION

Various embodiments of the present invention provide an improved system and method for the insertion of a conduit (such as an AAC conduit) that will significantly simplify the in vivo insertion of a graft into the beating cardiac apex or other tissue walls (such as other areas of the heart including the anterior, lateral, posterior walls of the left or right ventricle, the left or right atrium, the aortic wall, ascending, transverse, or descending, or other blood vessel walls), such that vascular conduit insertions (including AAC procedures) may be rendered far more attractive to clinicians. Because vascular conduits and systems of the present invention may be used to create alternate outflow tracts in "off-pump" procedures, the embodiments of the present invention may effectively reduce and/or negate the detrimental effects of both cardio-pulmonary by-pass (CPB) and global cardiac ischemia. Additionally, because some conduit embodiments of the present invention (for AAC procedures, for example) may be inserted into a ventricular or atrial free wall or cardiac apex, the conduction system of the heart may be avoided, along with the native coronary arteries and grafts from previous surgical revascularization. In some embodiments of the present invention, wherein the system is used to implant an AAC, a small size valve (19 to 21 mm for typical adult body surface areas) is usually adequate; as the effective postoperative orifice is the sum of the native and prosthetic aortic valves. Further, the present invention provides vascular conduits that may be compatible with newer generation biologic valves, such that valved conduit failure is far less likely. Various embodiments of the present invention may also provide general conduit devices (and systems for implanting) suitable for establishing fluid communication between opposing surfaces of tissue walls in a variety of applications, including the establishment of a fluid conduit through the tissue wall of a mammalian urinary bladder.

In one exemplary embodiment, a system is provided for implanting a conduit device (such as an AAC component) in a tissue wall having a first surface and an opposing second surface. According to some embodiments, the system comprises an outer tube defining a guide aperture extending axially through the outer tube and an attaching device extending from a distal end of said outer tube. The attaching device is configured for advancing along a helical path at least partially through the tissue wall such that at least a portion of the attaching device becomes disposed substantially between the first surface and the opposing second surface of the tissue wall when the outer tube is rotated relative to the first surface of the tissue wall. The attaching device, in some system embodiments, comprises at least one of a helical static coil and a helical elastic spring having a sharpened distal end adapted for piercing the tissue wall as the outer tube is rotated relative to the first surface of the tissue wall. According to some such embodiments, the attaching device may define a radially-expanding helix as the attaching device extends away from the distal end of the outer tube.

In some embodiments, the system also comprises a ring operably engaged about an outer surface of the outer tube and configured for cooperating with the attaching device such that at least a portion of the tissue wall is secured between the attaching device and the ring so as to operably engage said outer tube with the tissue wall. According to some such embodiments, the system may further comprise a plurality of ridges disposed on the outer surface of the outer tube. In such embodiments, the ring comprises at least one deformable pawl member operably engaged therewith for releasably engaging the plurality of ridges on the outer surface of the outer tube. In some other embodiments, the system may comprise threading on at least a portion of the outside surface of the outer tube and corresponding threading on at least a portion of an inside surface of the ring. The threading may be configured to cooperate for axially securing the ring relative to the outer tube. Furthermore, some system embodiments may further comprise a nut operably engaged about an outer surface of the outer tube and proximal to the ring. The nut may comprise threading on at least a portion on an inside surface thereof, wherein the threading may be configured for cooperating with the threading on at least a portion of the outside surface of the outer tube. Furthermore, the nut may be configured for cooperating with the ring to advance the ring towards the distal end of the outer tube.

In some embodiments, various system components, such as the outer tube and the ring, may be configured to conform to and/or establish a substantially fluid-tight seal with at least a portion a surface of the tissue wall. For example, in some embodiments, the system may comprise a sealing member operably engaged with a distal end of the ring. According to such embodiments, the sealing member may be configured for establishing a substantially fluid tight seal between the ring and the first surface of the tissue wall. In some embodiments, the system may be configured to cooperate and/or operably engage a tissue wall comprising a substantially curved tissue wall. According to some such embodiments, the ring may comprise a frusto-conical assembly configured for receiving at least a portion of the substantially curved tissue wall so as to form a substantially fluid-tight seal between the frusto-conical assembly and the tissue wall.

In some embodiments, the system further comprises an inner tube configured for insertion into the guide aperture defined by the outer tube. According to such embodiments, the inner tube defines a conduit aperture extending axially therethrough. Furthermore, in some such embodiments, the outer tube may comprise a first securing device operably engaged with a proximal end of the outer tube and the inner tube may comprise a complementary second securing device operably engaged with a proximal end of said inner tube. Thus, according to such embodiments, the second securing device may be configured for selectively operably engaging the first securing device so as to operably engage the inner tube with the outer tube to install and maintain the conduit.

In some embodiments, the system may also comprise a coring device configured for advancing through the conduit aperture defined by the inner tube and through the tissue wall to define an aperture therein by removing a tissue core. The coring device may be further configured for carrying the inner tube through the aperture such that the inner tube extends at least partially through the aperture so as to establish fluid communication between the first and second surfaces of the tissue wall. The coring device may define a coring bore extending axially therethrough and configured for receiving the tissue core removed by the coring device. In some embodiments, the coring device may further comprise a piercing rod slidably advancable and retractable within the coring bore. The piercing rod may further comprise a retrieval device operably engaged with a distal end thereof and configured for axially retaining the tissue core removed by the coring device. Thus, in some embodiments, the piercing rod may be configured for advancing so as to pierce the tissue wall prior to removal of the tissue core and/or retracting after removal of the tissue core such that the tissue core is retrievable via a proximal end of the coring device. In some such embodiments, the coring device may further comprise a handle operably engaged with the proximal end of the coring device. The handle may define a tissue core chamber in communication with the coring bore, the tissue core chamber configured for receiving the tissue core retrieved by the retraction of the piercing rod. Furthermore, in some such embodiments, at least a portion of the handle may comprise a transparent material such that the tissue core received therein is visible from a position outside the handle.

The various embodiments of the present invention may thus be configured for implanting a conduit device that is adapted for providing a conduit for a medical procedure. Such procedures may include, but are not limited to: bypass; cardiac valve repair or replacement; attachment of a ventricular assist device; establishment of an apicoaortic conduit (AAC) and combinations of such procedures.

Use of this new conduit device, system, and method will significantly improve the ease and safety of conduit insertion (such as the implantation of AAC devices, for example). For example, various embodiments of the present invention may allow the outer tube to be securely operably engaged with the tissue wall (due at least in part to the cooperation of the attaching device and the ring) prior to the removal of a tissue core to define an aperture in the tissue wall. Thus, portions of the system disclosed herein may define a guide aperture extending axially through the outer tube for receiving a coring device that may be configured to be capable of efficiently removing and retrieving a tissue core while substantially simultaneously operably engaging a inner tube in the guide aperture so as to establish fluid communication between first and second opposing surfaces of the tissue wall. As persons of ordinary skill in the art will readily appreciate, the various embodiments of the present invention may also be used in a minimally invasive, endoscopically assisted approach.

BRIEF DESCRIPTION OF THE DRAWINGS

Figure 1:
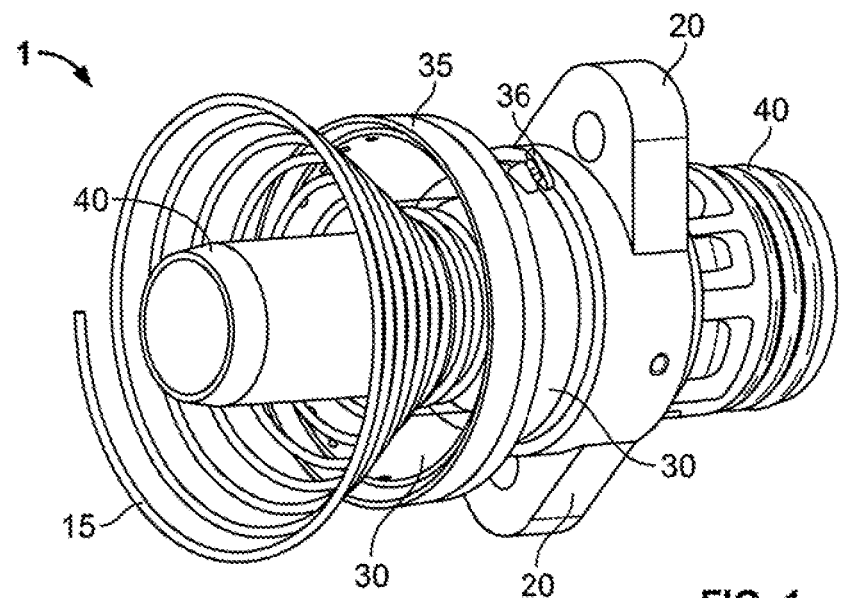
Figure 2:
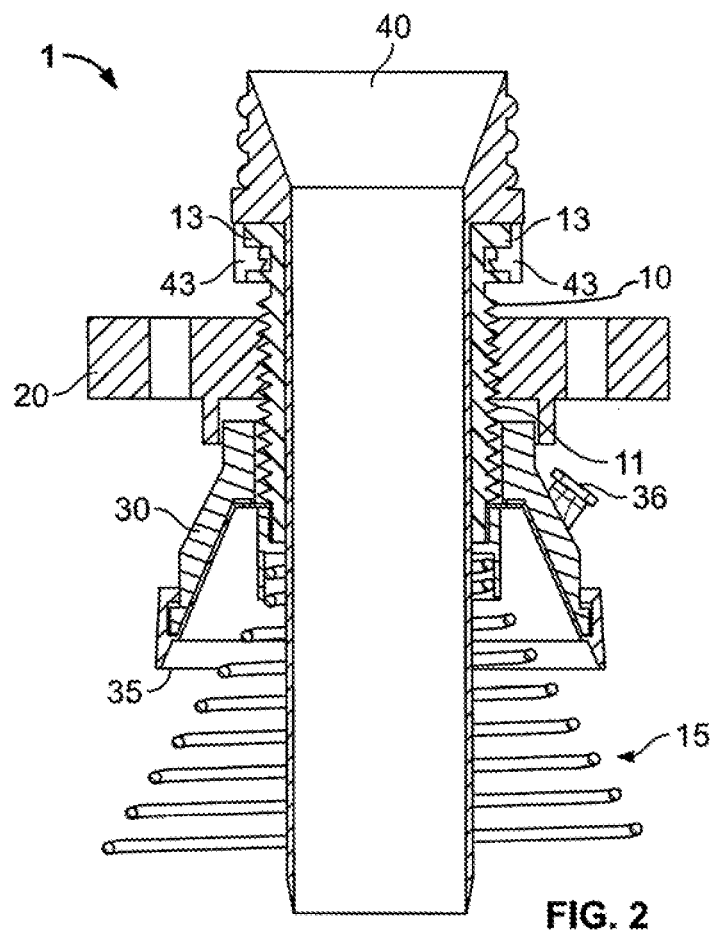
Figure 3:
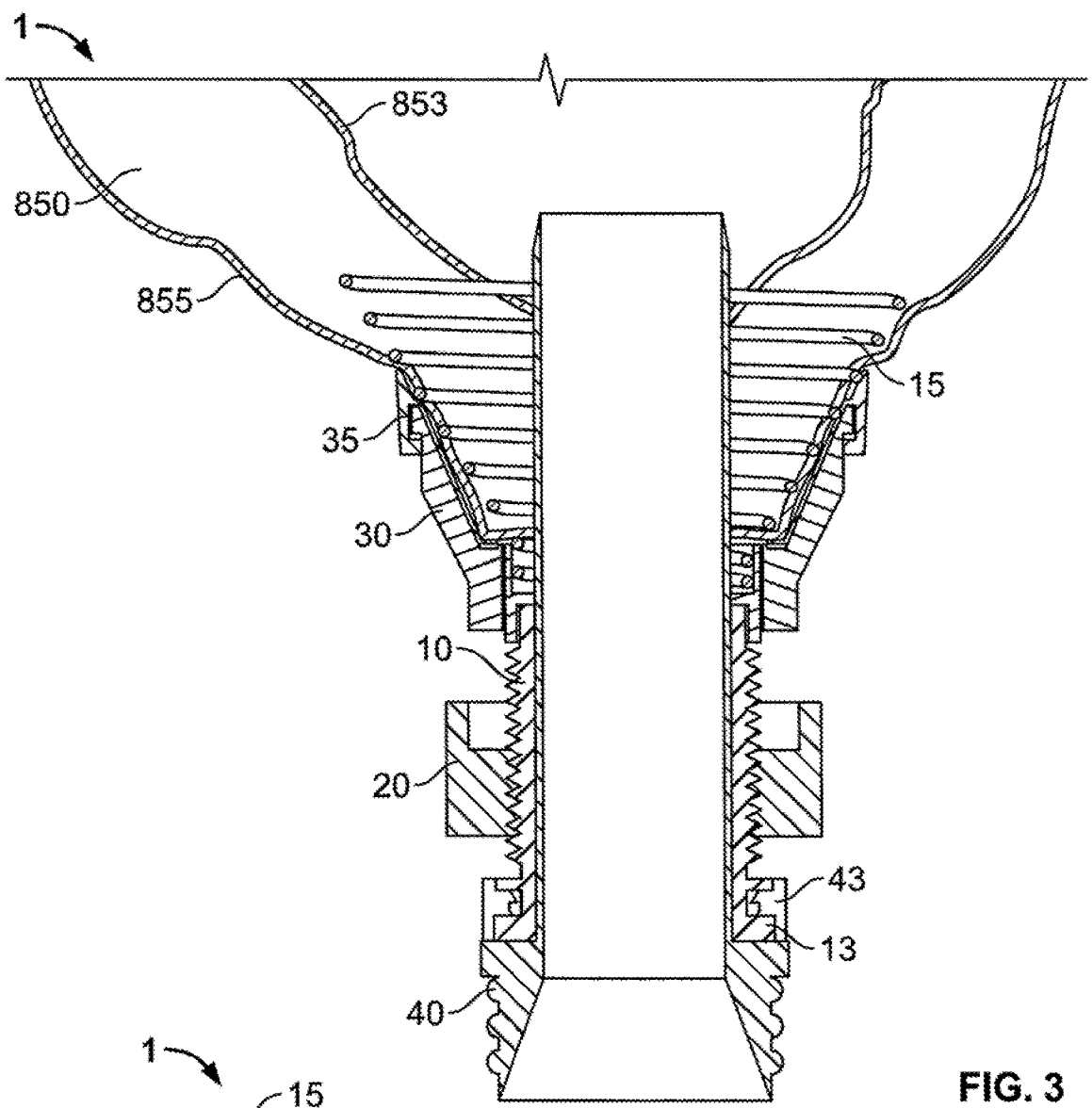
Figure 4:
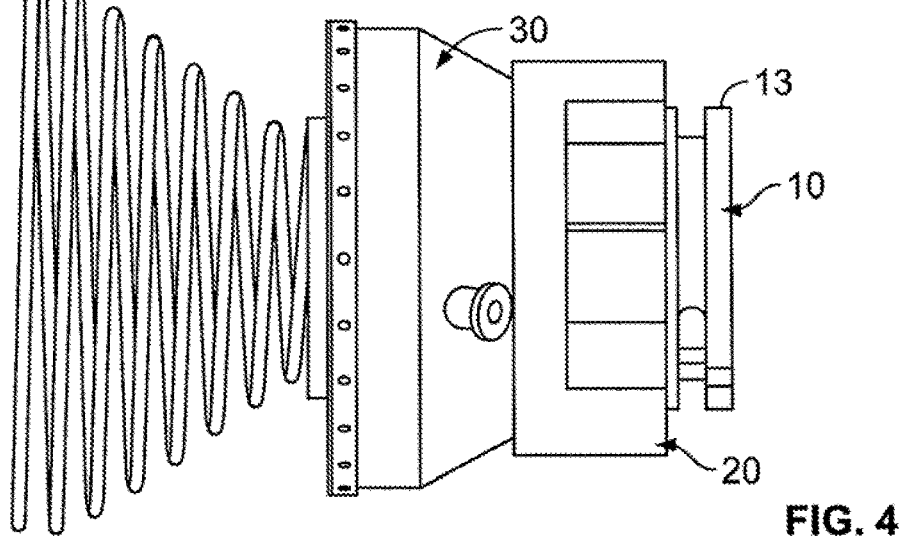
Figure 5A:
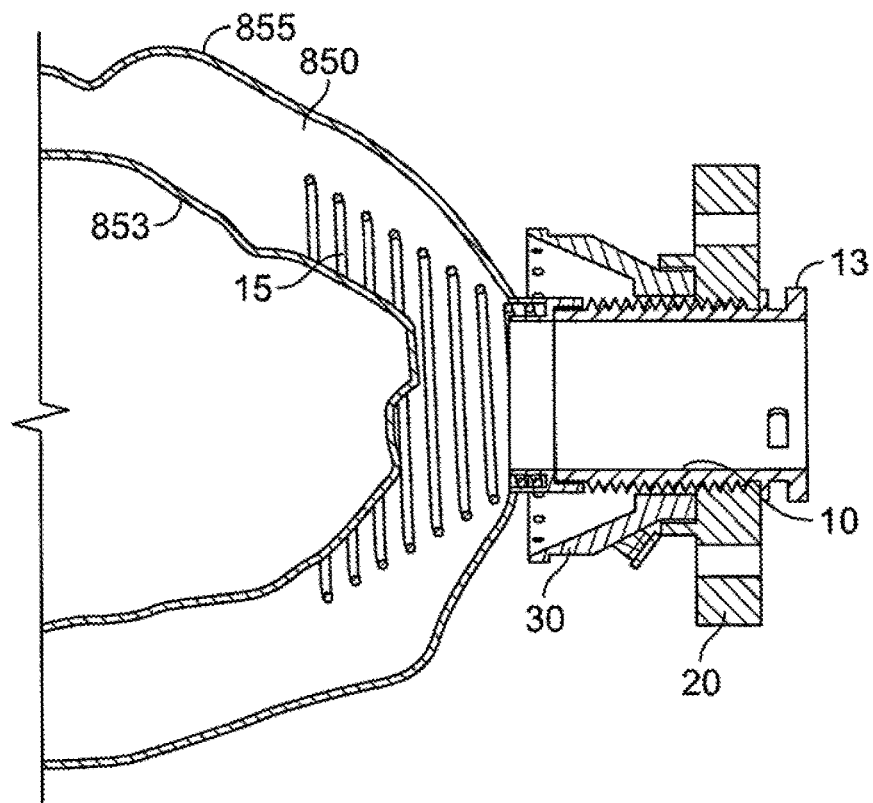
Figure 5B:
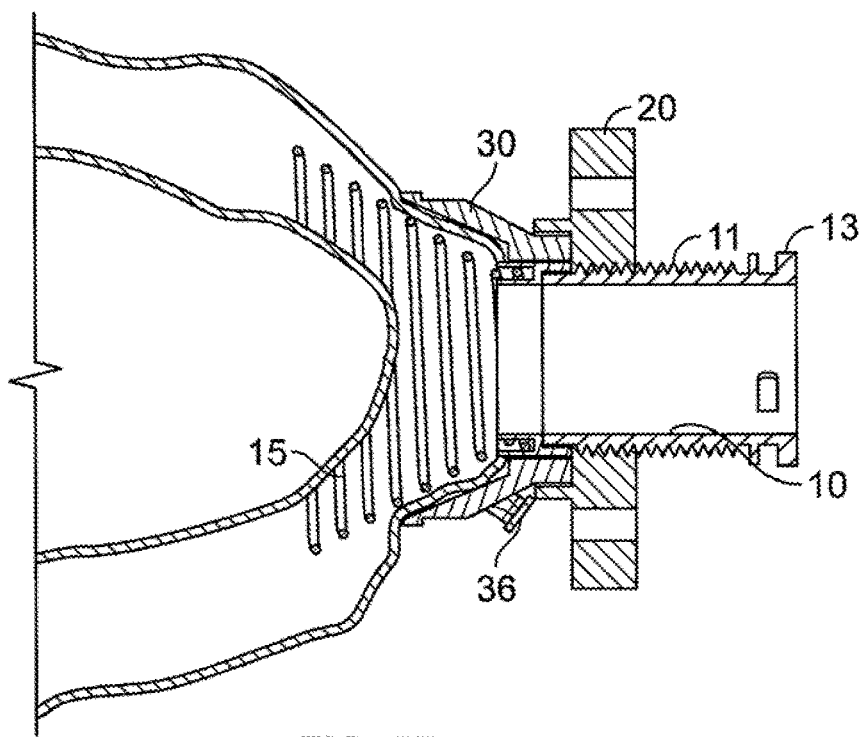
Figure 5D:
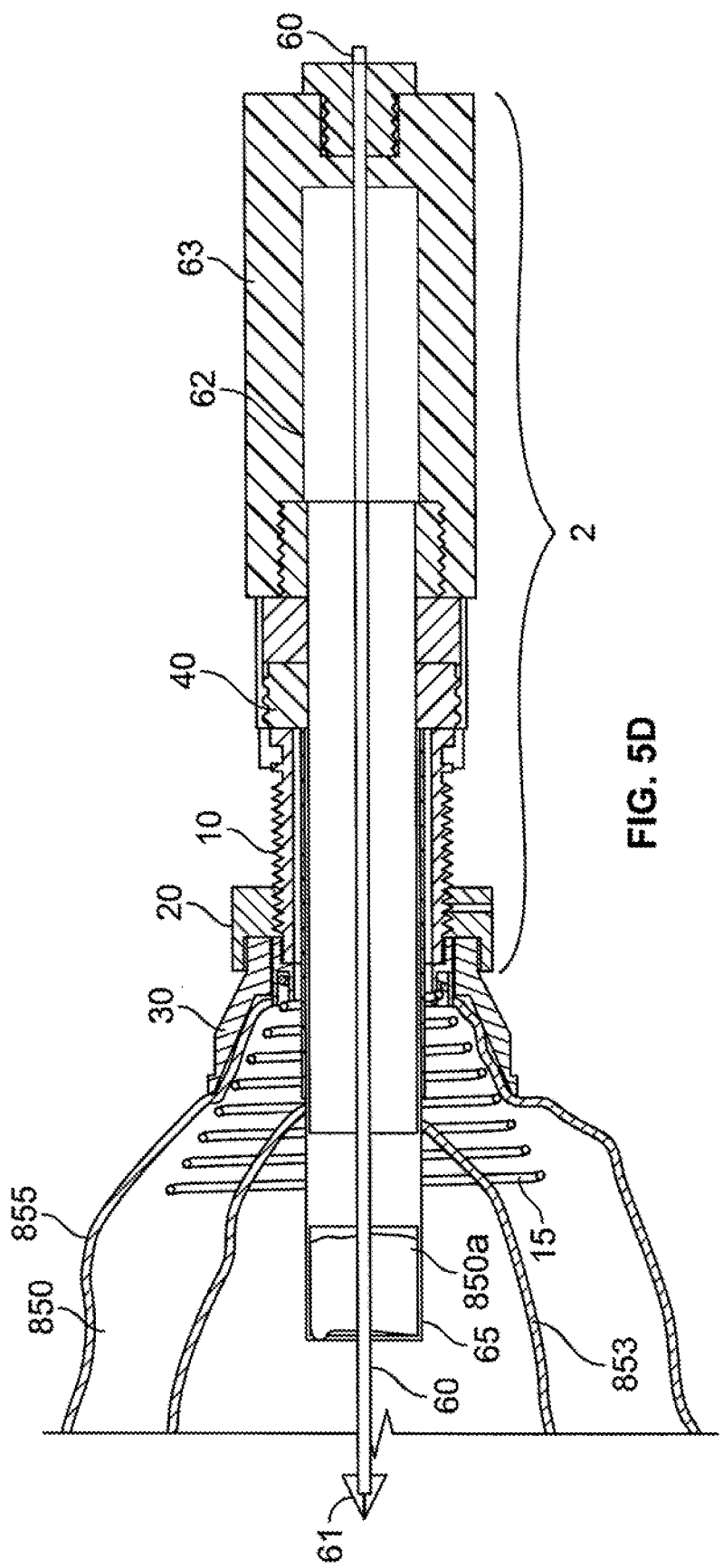
Figure 5E:
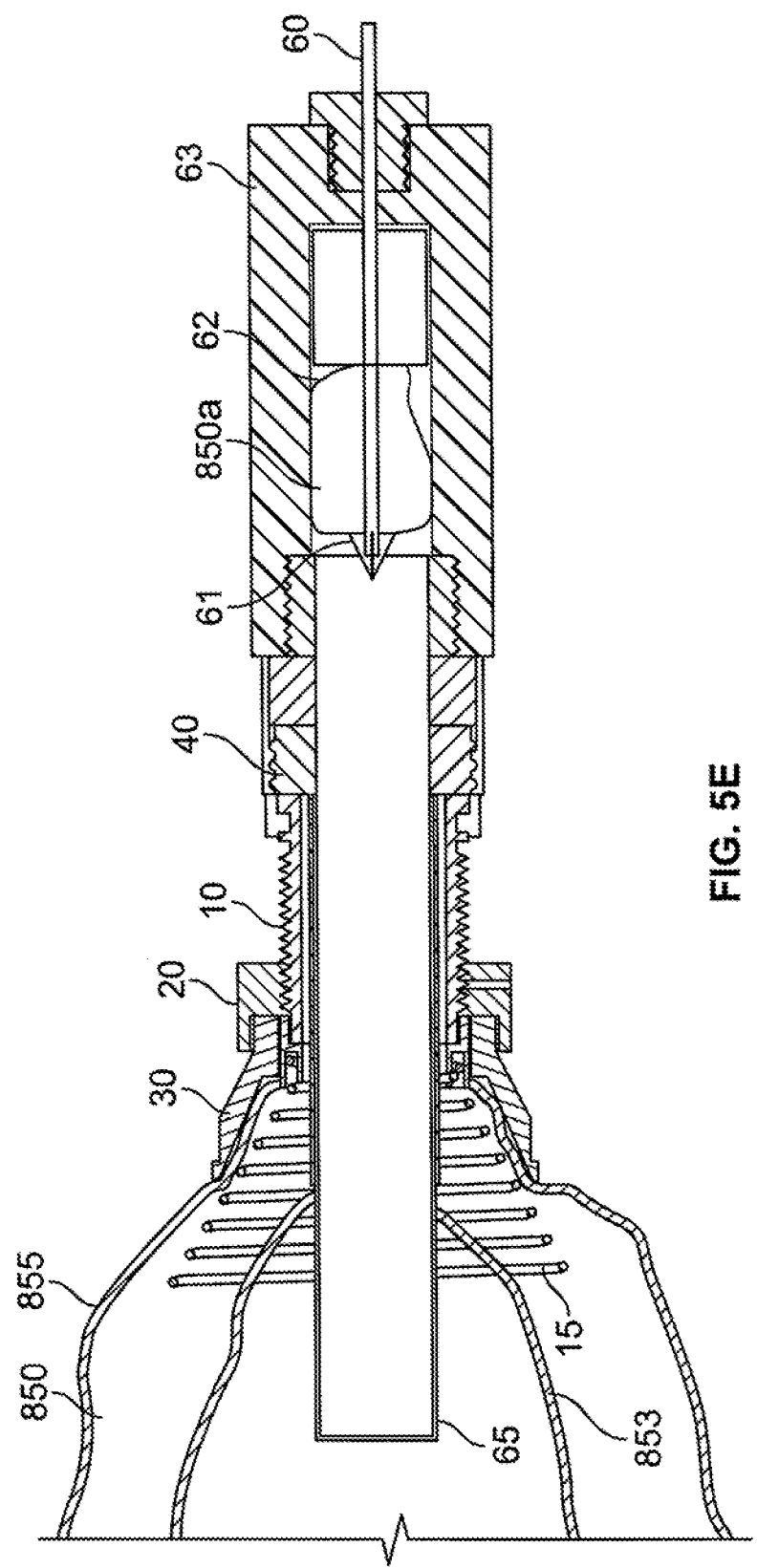
Figure 5F:
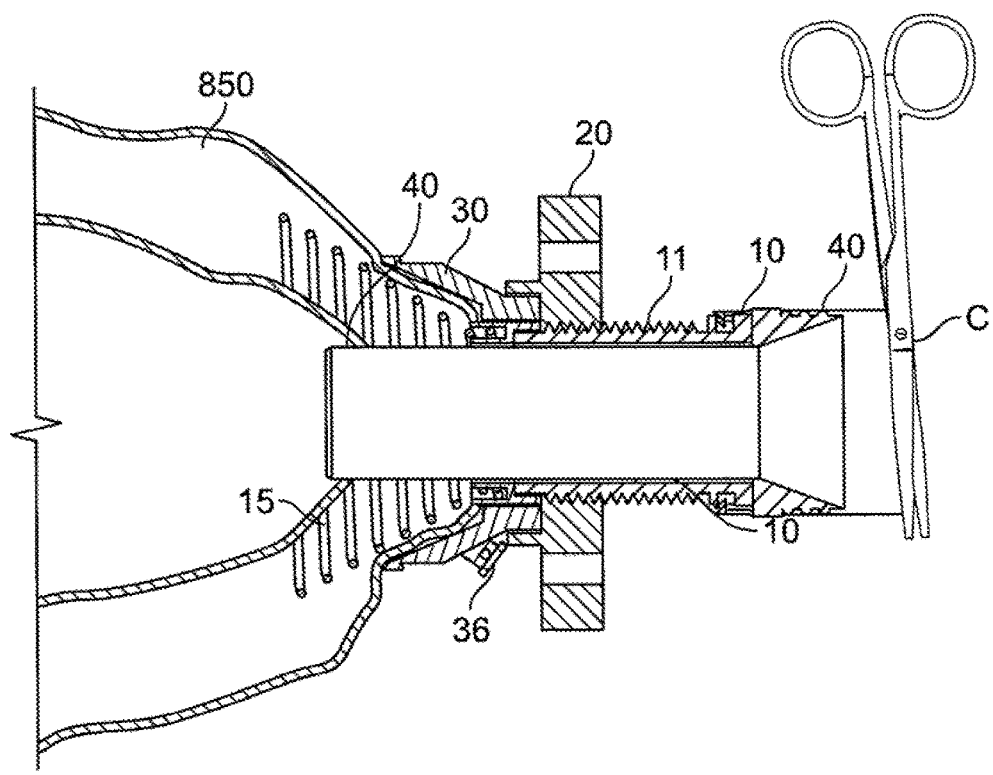
Figure 5G:
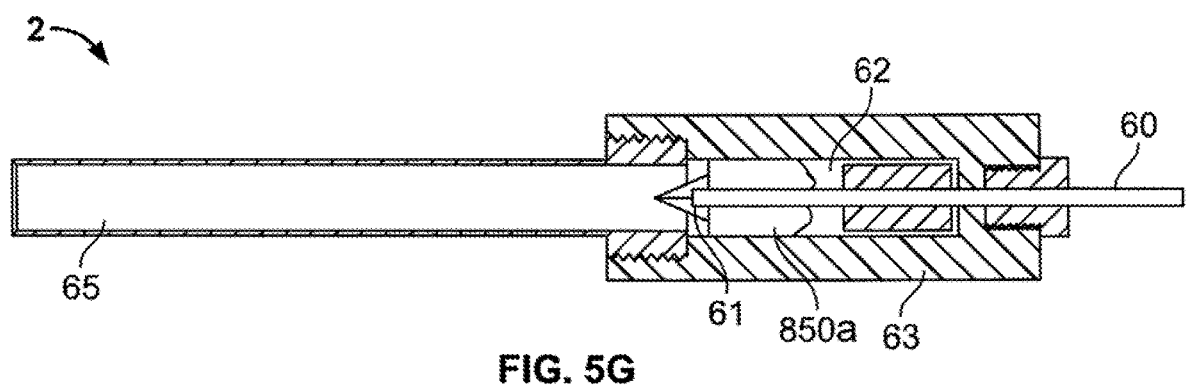
Figure 6:
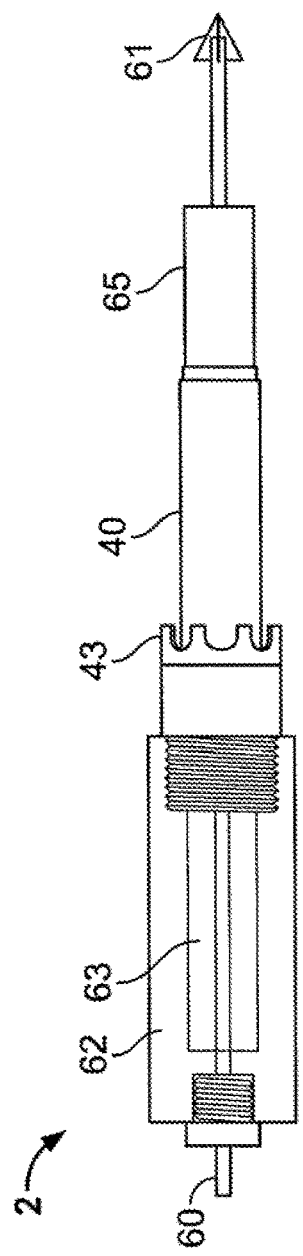
Figure 7:
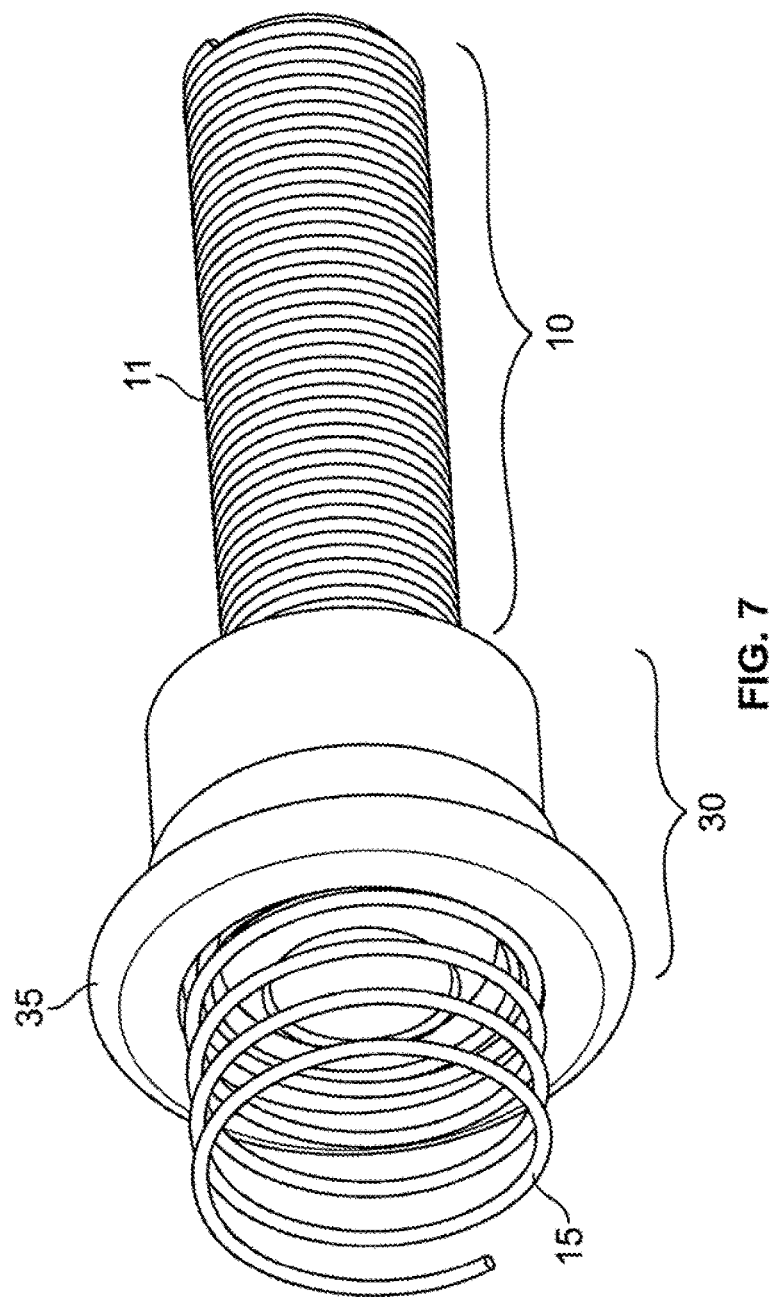

Having thus described various embodiments of the invention in general terms, reference will now be made to the accompanying drawings, which are not necessarily drawn to scale, and wherein:

FIG. 1 shows a non-limiting perspective view of an exemplary system for implanting a conduit device, according to one embodiment of the present invention;

FIG. 2 shows a non-limiting side cross-sectional view of an exemplary system for implanting a conduit device, according to one embodiment of the present invention;

FIG. 3 shows a non-limiting side cross-sectional view of an exemplary conduit device implanted in a tissue wall, according to one embodiment of the present invention;

FIG. 4 shows a non-limiting side view of an exemplary system for implanting a conduit device, according to one embodiment of the present invention;

FIGS. 5A-5G show an exemplary set of views of the installation of a conduit device using an exemplary system, according to one embodiment of the present invention;

FIG. 5A shows a non-limiting side cross-sectional view of an exemplary system for implanting a conduit device comprising an attaching device at least partially implanted in a tissue wall, according to one embodiment of the present invention;

FIG. 5B shows a non-limiting side cross-sectional view of an exemplary system for implanting a conduit device comprising an attaching device and a ring cooperating to secure at least a portion of the tissue wall between the attaching device and the ring so as to operably engage said outer tube with the tissue wall, according to one embodiment of the present invention;

FIG. 5C shows a non-limiting side cross-sectional view of an exemplary system for implanting a conduit device comprising a coring device carrying an inner tube configured for insertion into a guide aperture defined by the outer tube, wherein the coring device is advanced at least partially through the tissue wall so as to remove a tissue core thereof, according to one embodiment of the present invention;

FIG. 5D shows a non-limiting side cross-sectional view of an exemplary system for implanting a conduit device comprising a coring device carrying an inner tube configured for insertion into a guide aperture defined by the outer tube, wherein the coring bore defined by the coring device contains a tissue core removed from the tissue wall, according to one embodiment of the present invention;

FIG. 5E shows a non-limiting side cross-sectional view of an exemplary system for implanting a conduit device comprising a coring device carrying an inner tube configured for insertion into a guide aperture defined by the outer tube, wherein a piercing rod is retracted through the coring bore after removal of the tissue core such that the tissue core is retrievable via a proximal end of the coring device, according to one embodiment of the present invention;

FIG. 5F shows a non-limiting side cross-sectional view of an exemplary system for implanting a conduit device, wherein the outer tube and inner tube are installed in the tissue wall so as to establish fluid communication between the first and second surfaces of the tissue wall, according to one embodiment of the present invention;

FIG. 5G shows a non-limiting side cross-sectional view of an exemplary coring device, wherein a handle operably engaged with a proximal end of the coring device contains a tissue core removed from the tissue wall by the coring device, according to one embodiment of the present invention;

FIG. 6 shows a non-limiting side view of an exemplary coring device carrying an inner tube configured for insertion into a guide aperture defined by the outer tube, according to one embodiment of the present invention; and FIG. 7 shows a non-limiting perspective view of an exemplary conduit device comprising an attaching device comprising a helical spring, according to one embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements Like numbers refer to like elements throughout. The singular forms "a," "an," and "the" include plural referents unless the context clearly dictates otherwise.

Although some embodiments of the invention described herein are directed to a conduit device 1 (see FIGS. 1 and 7, for example) and a system for implanting such a device to form an apicoaortic connector (AAC) between the cardiac apex and the aorta, it will be appreciated by one skilled in the art that the invention is not so limited. For example, aspects of the conduit device 1 and systems of the present invention can also be used to establish and/or maintain conduits in a variety of tissue structures using minimally-invasive and/or invasive delivery techniques. Furthermore, while the embodiments of the invention described herein are directed to the thoracoscopic implantation of the conduit device to form at least one port for establishing an AAC, it should be understood that the system and/or vascular conduit device embodiments of the present invention may be used to establish valved and/or open conduits (including bypass conduits) to augment native blood vessels in order to treat a variety of vascular conditions including, but not limited to: aortic valvular disease, congestive heart failure, left ventricle outflow tract obstructions (LVOTO), peripheral arterial obstructions, small vessel obstructions, and/or other conditions. Furthermore, the vascular conduit device and system of the present invention may also be used to establish a port for inter¬ventricular repairs such as, for example, valve repair and/or replacement or ablation procedures. Thus, the conduit device 1 described in further detail below may also comprise a threaded fluid-tight cap, and/or a cap having at least one pawl member (for engaging corresponding ridges defined on an outer surface of the conduit device 1) for selectively sealing a proximal end of the conduit device 1 such that the inner tube 40 thereof may serve as a re-usable port for repairing and/or treating diseased portions of the cardiac anatomy. Furthermore, the conduit device 1 and system embodiments of the present invention may also be used to implant a conduit and/or port for left ventricular assist devices.

It should be further understood that various embodiments of the conduit device 1 described herein may also be utilized to establish fluid communication between opposing surfaces of a variety of tissue walls and/or anatomical structures. For example, in some embodiments, the conduit device 1 and system for implanting described herein may be used to establish a conduit (and consequently fluid communication) between opposing surfaces of a wall of an anatomical structure that may include, but is not limited to: a urinary bladder; a gall bladder; a diaphragm; a thoracic cavity; an abdominal cavity; an intestinal structure; a cecal cavity; and other tissue wall structures.

It should be understood that the various conduit device 1 components described herein (see, for example, the components shown in FIG. 1) may comprise a variety of biocompatible materials including, but not limited to: stainless steel; titanium substantially rigid biocompatible polymers; elastomeric biocompatible polymers; and combinations of such materials. For example, in some embodiments, the outer tube 10, ring 30, nut 20, and inner tube 40 may comprise substantially rigid biocompatible polymers. In some embodiments, the attaching device 15 may comprise a biocompatible metal and/or metal alloy that may be embedded substantially within and/or operably engaged with an injection-molded polymer used to form the outer tube 10. Furthermore, as described further herein, some embodiments of the present invention may further comprise a sealing member 35 operably engaged with a distal end of the ring 30. In such embodiments, the sealing member 35 may comprise a substantially compliant biocompatible polymer (such as an elastomeric polymer) that may be suitable for establishing a substantially fluid tight seal between the ring 30 a surface of the tissue wall 850. Similarly, the various components of the coring device 2 described herein may also comprise a combination of biocompatible materials suitable for removing and retaining the tissue core 850a in order to define an aperture in the tissue wall 850 such that the inner tube 40 may be installed to establish fluid communication between the opposing first and second surfaces 855, 853 of the tissue wall 850 (as shown in FIG. 3, for example).

FIG. 3 shows some exemplary components of a system for implanting a conduit device 1 in a tissue wall 850 having a first surface 855 and an opposing second surface 853. As shown generally in FIGS. 1 and 2, such a system may comprise an outer tube 10 defining a guide aperture extending axially therethrough and an attaching device 15 extending from a distal end of the outer tube 10. As shown in FIG. 3, for example, the attaching device 15 may be configured for advancing along a helical path at least partially through the tissue wall 850 such that at least a portion of the attaching device 15 becomes disposed substantially between the first surface 855 and the opposing second surface 853 of the tissue wall 850 when the outer tube 10 is rotated relative to the first surface 855 of the tissue wall 850. As shown generally in FIG. 2, the attaching device 15 may be integrally formed within the outer tube 10. For example, the attaching device 15 may, in some embodiments, be placed at least partially in a mold such that the polymeric or other components of the outer tube 10 may be molded substantially around at least a portion of the attaching device 15 (which may comprise a static coil and/or elastic spring, as described further herein). In other embodiments, the attaching device 15 may be operably engaged with at least a portion of the outer tube 10 via adhesive, RF welding, and/or other attachment methods that may be suitable for securely operably engaging the attaching device 15 to the outer tube 10.

The attaching device 15 may comprise, in some embodiments, a helical static coil having a sharpened distal end adapted for piercing the tissue wall 850 as the outer tube 10 is rotated relative to the first surface 855 of the tissue wall 850. In other embodiments, the attaching device 15 may comprise a helical elastic spring having a sharpened end adapted for piercing the tissue wall 850 as the outer tube 10 is rotated relative to the first surface 855 of the tissue wall 850. In some embodiments, as shown in FIG. 4, wherein the attaching device 15 comprises a helical spring and/or coil, the spring and/or coil may device a radially-expanding helix as the attaching device 15 extends away from the distal end of the outer tube 10. In some embodiments, wherein the attaching device comprises a conical and/or "radially-expanding" helix, the attaching device 15 may act to compress at least a portion of the tissue wall 850 radially inward and towards an outer surface of the inner tube 40 so as to establish a substantially fluid-tight seal between the outer surface of the inner tube 40 and the portion of the tissue wall 850 that has been urged radially inward. Furthermore, in some such embodiments, the radially-expanding helix of the attaching device 15 may correspond, for example, to a ring 30 comprising a frusto-conical assembly configured for receiving at least a portion of a substantially curved tissue wall 850 (see, for example, FIG. 5B) so as to form a substantially fluid-tight seal between the frusto-conical assembly of the ring 30 and the tissue wall 850.

In other embodiments, as shown generally in FIG. 7, the attaching device 15 may comprise a helical spring and/or coil having a substantially constant helical diameter as the attaching device 15 extends away from the distal end of the outer tube 10. The substantially consistent helical diameter of the attaching device 15 shown generally in FIG. 7 may be useful for operably engaging the outer tube 10 with a substantially flat tissue wall 850. Furthermore, as shown generally in FIG. 7, in some embodiments, the corresponding ring 30 (and the corresponding sealing member 35 that may be operably engaged therewith) may also be configured to provide a substantially flat and/or disc-ishaped sealing surface that may be suitable for seating on and/or establishing a substantially fluid-tight seal with a substantially flat first tissue surface 855 that may surround an aperture defined in a correspondingly flat tissue wall 850.

As described herein, the system may further comprise a ring 30 operably engaged about an outer surface of the outer tube 10. As shown generally in FIGS. 3 and 5B, the ring 30 may be configured for cooperating with the attaching device 15 such that at least a portion of the tissue wall 850 is secured between the attaching device 15 and the ring 30 so as to operably engage the outer tube 10 with the tissue wall 850. Some embodiments may further comprise a plurality of ridges 11 and/or threads disposed on the outer surface of the outer tube 10. According to such embodiments, the ring 30 may comprise at least one deformable pawl member configured for releasably engaging the plurality of ridges 11 disposed on the outer surface of the outer tube 10. Other embodiments (as shown generally in FIG. 2, for example), may also further comprise threading 11 on at least a portion of the outside surface of the outer tube 10 and corresponding threading on at least a portion of an inside surface of the ring 30. The threading 11 (and corresponding threading on the inner surface of the ring 30) may be being configured to cooperate for axially securing the ring 30 relative to the outer tube 10. As shown generally in FIGS. 5A-5B, some embodiments may further comprise a nut 20 operably engaged about an outer surface of the outer tube 10 and proximal to the ring 30. According to such embodiments, the nut 20 may comprise threading on at least a portion on an inside surface of the nut 20. The threading disposed on the inside surface of the nut 20 may be configured for cooperating with the threading 11 on at least a portion of the outside surface of the outer tube 11 for axially securing the nut 20 relative to the outer tube 10 and the adjacent ring 20. As shown in FIGS. 5A-5B, the nut 20 may be configured for cooperating with the ring 30 to advance the ring 30 towards the distal end of the outer tube 10. As shown generally in FIGS. 5A-5B, the attaching device 15 may provide counter-traction so as to allow for the rotation (and resulting advancement) of the nut 20 (and the ring 30 disposed distally thereto) such that rotation of the nut 20 (and the corresponding movement of the ring 30 toward the first tissue surface 855) may draw at least a portion of the tissue wall 850 into engagement with an inner surface of the ring 30 such that the conduit device 1 (and particularly the outer tube 10 thereof) is stabilized, engaged in a substantially fluid tight seal, and/or operably engaged with respect to the tissue wall 850 prior to the use of a coring device 2 for removing a tissue core 850a via the guide aperture defined axially through the outer tube 10.

In order to ensure that the ring 30 forms a substantially fluid-tight seal with the first surface 855 of the tissue wall 850 about the aperture defined therein, some embodiments (as shown in FIG. 1, for example) may further comprise a sealing member 35 operably engaged with a distal end of the ring 30. The sealing member 35 may comprise, for example, a gasket or other elastomeric component configured for establishing a substantially fluid tight seal between the ring 30 and the first surface 855 of the tissue wall 855. As described herein, some embodiments of the present invention may be configured for establishing fluid communication between the opposing sides of the walls of a mammalian heart (such as the ventricular apex, for example). In such embodiments, the conduit device 1 may be required to be operably engaged with a substantially curved tissue wall 850 (see FIG. 5A, for example). In such embodiments, the ring 30 may comprise a frusto-conical assembly configured for receiving at least a portion of the substantially curved tissue wall 850 so as to form a substantially fluid-tight seal between the frusto-conical assembly of the ring 30 and the tissue wall 850. As shown, for example, in FIG. 5B, in some embodiments, the ring 30 may be urged towards a distal end of the outer tube 10 by the rotation of a nut 20 about threading 11 disposed on an outer surface of the outer tube 10. Thus, according to some such embodiments, the cooperation of the attaching device 15 (which may comprise a piercing helical spring and/or coil, for example) with the ring 30 may act to draw at least a portion of the curved tissue wall 850 into the frusto-conical assembly of the ring 30 such that a substantially fluid-tight seal may be formed and maintained between the frusto-conical assembly of the ring 30 and the tissue wall 850. In some conduit device 1 embodiments, as shown generally in FIG. 2, the ring 30 may comprise a seal testing aperture 36 that may allow a clinician to selectively test whether or not a substantially fluid-tight seal has been established between the ring 30 and the first surface 855 of the tissue wall 850 when the ring 30 is moved towards the distal end of the outer tube 10 and into engagement with the tissue wall 850. For example, a clinician may operably engage a fluid source (such as a saline solution bag) with the seal testing aperture 36 (which may comprises a luer lock connector or other connector for operably engaging the fluid source) and introducing a fluid via seal testing aperture 36 and observing the interface between the ring 30 and the first surface 855 of the tissue wall 850 to see if any substantial amount of fluid emerges. If no fluid is readily visible, a clinician may be reasonably assured that the seal formed between the ring 30 and the tissue wall 850 is substantially fluid-tight. By assessing the seal formed between the ring 30 and the tissue wall 850, a clinician may determine if it is medically safe to introduce the coring device 2 via the guide conduit defined in the outer tube 10 (i.e. determine if blood loss is likely to occur between the ring 30 and the first surface 855 of the tissue wall 850 when the coring device 2 (and the coring cylinder 65 thereof) is advanced through the tissue wall 850 as shown in FIG. 5C).

In some embodiments, the seal testing aperture 36 may also serve an alternative function for rotationally securing the ring 30 relative to and the first surface 855 of the tissue wall 850. For example, a clinician may insert a needle and/or other elongate spike through the seal testing aperture 36 defined in the ring 30 and substantially into the tissue wall 850. The interaction of the needle and/or spike with the ring 30 (via the seal testing aperture 36) and the tissue wall 850 may thus reduce a chance that the ring 30 (and the helical attaching device 15 extending from the outer tube 10) are rotatable relative to the tissue wall 850 such that the ring 30 and the helical attaching device 15 may be less prone to "backing out" of the tissue wall 850 once the seal is established between the ring 30 and the first surface 855 of the tissue wall 850.

In some additional embodiments, as shown generally in FIG. 7, the ring 30 (and/or the sealing member 35 that may be operably engaged therewith) may define a substantially flat and/or disc-shaped annular sealing surface that may be configured for establishing a substantially fluid-tight seal between the ring 30 and a substantially flat first tissue surface 855 about an aperture defined in the tissue wall 850.

Referring to FIG. 5C, for example, some embodiments may further comprise an inner tube 40 defining a conduit aperture extending axially therethrough. The inner tube 40 may be configured for insertion into the guide aperture defined by the outer tube 10. In some embodiments, as shown in FIG. 6, the inner tube 40 may be carried by a coring device 2 that may be advanced through the guide aperture defined by the outer tube 10 and configured for substantially simultaneously removing a tissue core 850a to define an aperture in the tissue wall 850 and operably engaging the inner tube 40 with the outer tube 10 so as to establish and/or maintain a reliable and engageable pathway for fluid communication between the first and second surfaces 855, 853 of the tissue wall 850. In order to facilitate the secure engagement of the outer tube 10 with the inner tube 40, some conduit device 1 embodiments may comprise a first securing device 13 operably engaged with a proximal end of the outer tube 10 and a complementary second securing device 43 operably engaged with a proximal end of the inner tube 40. According to such embodiments, as shown generally in FIG. 2, the second securing device 43 may be configured for selectively operably engaging the first securing device 13 so as to operably engage the inner tube 40 with the outer tube 10. As shown generally in FIG. 6, the second securing device 43 may comprise one or more deformable pawls configured for selectively operably engaging the first securing device 13 as shown in FIG. 2 (wherein the first securing device 13 comprises one or more ridges disposed on a proximal portion of the outer surface of the outer tube 10).

As shown generally in FIG. 6, some system embodiments for installing a conduit device 1 may further comprise a coring device 2 configured for advancing through the conduit aperture defined by the inner tube 40 and through the tissue wall 850 to define an aperture therein by removing a tissue core 850a (see FIG. 5D, for example, showing the coring device 2 removing a tissue core 850a and collecting the tissue core 850a in a coring bore defined by a coring cylinder 65. As shown generally in FIGS. 5C and 6, the coring device 2 may be further configured for carrying the inner tube 40 through the aperture such that the inner tube 40 extends at least partially through the aperture (see FIG. 5F, for example) so as to establish fluid communication between the first 855 and second 853 surfaces of the tissue wall 850. In some embodiments, as shown in the cross-sectional side view of FIG. 5D, the coring device 2 (and/or the coring cylinder 65 thereof) defines a coring bore extending axially therethrough configured for receiving the tissue core 850a removed by the coring cylinder 65.

As shown in FIGS. 5C-5E, the coring device 2 may also comprise a piercing rod 60 slidably advancable and retractable within the coring bore defined by the coring device 2. The piercing rod 60 may further comprise a retrieval device 61 operably engaged with a distal end thereof and configured for axially retaining the tissue core 850a removed by the coring cylinder 65. In various embodiments, the retrieval device 61 may include, but is not limited to: a barb; a hook; corkscrew; expandable balloon; a self-expanding structure; and/or other device configured for initially piercing the tissue wall 850 so as to be capable of retrieving the tissue core 850a removed by the coring device 2 as described further herein. As shown generally in FIG. 5C, the piercing rod 60 may be configured for advancing so as to pierce the tissue wall 850 prior to removal of the tissue core 850a (i.e. prior to the advancement of the coring cylinder 65 through the tissue wall 850). Furthermore, as shown generally in FIG. 5E, the piercing rod 60 may be further configured for retracting after removal of the tissue core 850a such that the tissue core 850a is retrievable via a proximal end of the coring device 2. In some system embodiments for installing a conduit device 1, the coring device 2 may further comprise a handle 63 operably engaged with a proximal end of the coring device 2 (and/or a proximal end of the coring cylinder 65). According to such embodiments, as shown generally in FIG. 6, the handle 63 may define a tissue core chamber 62 in communication with the coring bore defined by the coring cylinder 65. As shown in FIG. 5E, the tissue core chamber 62 may thus be configured for receiving the tissue core 850a retrieved by retraction of the piercing rod 60 (and the retrieval device 61 operably engaged with a distal end thereof). In order to allow a clinician to positively identify and/or confirm the removal and retraction of the tissue core 850a, in some system embodiments at least a portion of the handle 63 may be provided with a substantially transparent material (such as a transparent polycarbonate polymer, for example) such that the tissue core 850a received by the tissue core chamber 62 may be visible (to a clinician or an endoscopic imaging device, for example) from a position substantially outside the handle 63.

FIGS. 5A-5G illustrate the various steps involved in the utilization of one embodiment of the system of the present invention for installing a conduit device 1 in a tissue wall 850 (such as the ventricular apex). It should be understood that various embodiments of the present invention may be utilized for installing the conduit device 1 for use in medical procedures that may include, but are not limited to: bypass; cardiac valve repair or replacement; attachment of a ventricular assist device; and combinations of such procedures. As shown in FIG. 5A, an exemplary process for installing a conduit device 1 may begin with the implantation of the attaching device 15 in the tissue wall 850. As described herein, the attaching device 15 may comprise a helical spring and/or coil configured for advancing along a helical path at least partially through the tissue wall 850 such that at least a portion of the attaching device 850 becomes disposed substantially between the first surface 855 and the opposing second surface 853 of the tissue wall 850 when the outer tube 10 is rotated relative to the first surface 855 of the tissue wall 850. In some embodiments, the attaching device 15 may be sized such that the axial length of the attaching device 15 does not extend substantially distal to the second surface 853 of the tissue wall 850.

In some embodiments, wherein the attaching device comprises a conical and/or "radially-expanding" helix, the attaching device 15 may act to compress at least a portion of the tissue wall 850 radially inward and towards an outer surface of the inner tube 40 so as to establish a substantially fluid-tight seal between the outer surface of the inner tube 40 and the portion of the tissue wall 850 that has been urged radially inward by the conical and/or radially-expanding helix of the attaching device 15. Furthermore, in embodiments wherein the attaching device 15 comprises a conical and/or "radially-expanding" helix, the attaching device 15 may act to compress at least a portion of the tissue wall 850 radially inward such that the portion of the tissue wall 850 may be more readily received by ring 30 (which may comprise a frusto-conical structure configured for receiving the compressed portion of the tissue wall 850). As shown in FIG. 5B, the conduit device 1 installation process may continue with the advancement and/or tightening of the ring 30 towards a distal end of the outer tube 10. As described herein, some conduit device 1 embodiments of the present invention may comprise a nut 20 operably engaged about an outer surface of the outer tube 10 proximal to the ring 30. In some such embodiments, the nut 20 may comprise threading on at least a portion on an inside surface thereof, wherein the threading is configured for cooperating with the threading 11 on at least a portion of the outside surface of the outer tube 10. The nut 20 may thus be configured to cooperate with the ring 30 to advance the ring 30 towards the distal end of the outer tube 10, and therefore into contact with the first surface 855 of the tissue wall 850. As shown generally in FIG. 5B, once the nut 20 and ring 30 are advanced distally (which may be accomplished by hand-tightening the nut 20), the ring 30 may cooperate with the attaching device 15 such that at least a portion of the tissue wall 850 is secured between the attaching device 15 and the ring 30 so as to securely operably engage the outer tube 10 with the tissue wall 850.

As shown in FIG. 5C, once the outer tube 10 is stabilized relative to the tissue wall 850, a coring device 2 (which, in some embodiments, as shown in FIG. 6, may be configured for carrying an inner tube 40), may be inserted into the guide aperture defined axially within the outer tube 10. As described herein with respect to FIG. 6, the coring device 2 may comprise a coring cylinder 65 configured for advancing through the conduit aperture defined by the inner tube 40 and through the tissue wall 850 to define an aperture therein by removing a tissue core 850a (see FIG. 5D, for example). Referring again to FIG. 5C, some embodiments may further comprise a piercing rod 60 slidably advancable and retractable within the coring bore defined by the coring cylinder 65. The piercing rod 60 may comprise, in some embodiments, an elongate proximal end that may be manipulated (i.e. extended and/or retracted) by a clinician in order to initially pierce the tissue wall 850 and/or retract the tissue core 850a removed therefrom (as described further herein). As shown in FIGS. 5D and 5E, the piercing rod 60 may further comprise a retrieval device 61 operably engaged with a distal end thereof and configured for axially retaining the tissue core 850a removed by the coring cylinder 65. The piercing rod 60 may be configured for advancing so as to pierce the tissue wall 850 prior to removal of the tissue core 850a (i.e. prior to advancement of the coring cylinder 65). Furthermore, as shown in FIG. 5E, the piercing rod 60 may be further configured for retracting after removal of the tissue core 850a such that the tissue core 850a is retrievable via a proximal end of the coring device 2.

As shown in FIGS. 5D and 6, the coring device 2 may be further configured for carrying the inner tube 40 through the aperture such that the inner tube 40 extends at least partially through the aperture so as to establish fluid communication between the first and second surfaces 855, 853 of the tissue wall 850 (see also, FIG. 3, for example). As described herein, with respect to various conduit device 1 embodiments of the present invention the outer tube 10 may comprise a first securing device 13 operably engaged with a proximal end thereof and the inner tube 40 (carried, for example, by the coring device 2 into position relative to the outer tube 10) may comprise a complementary second securing device 43 operably engaged with a proximal end thereof. As shown generally in FIG. 3, the second securing device 43 (which may comprise a deformable pawl, for example) may be configured for selectively operably engaging the first securing device 13 (which may comprise a complementary at least one ridge disposed on an outer surface of the outer tube 10) so as to positively and securely operably engage the inner tube 40 with the outer tube 10.

Referring again to FIG. 5E, the coring device 2 may, in some embodiments, comprise a handle 63 operably engaged with a proximal end of the coring device 2. As described herein, the handle 63 may define a tissue core chamber 62 in communication with the coring bore defined, for example, by the coring cylinder 65. The tissue core chamber 62 may thus be configured for receiving the tissue core 850a retrieved by retraction of the piercing rod 60 (and the retrieval device 61 operably engaged with a distal end thereof). In some embodiments, the coring device 2 may also define a fill aperture configured for operably engaging a source of saline solution or other fluid that may be used to substantially flood the coring bore defined by the coring cylinder 65 and the tissue core chamber 62 so as to reduce the chance of introducing gas bubbles (i.e. air bubbles) into an interior chamber defined by the tissue wall 850 when the coring device 2 is introduced via the outer tube 10.

As described generally herein with regard to the various system embodiments of the present invention, the conduit device 1 installation process may advantageously allow a clinician to visually confirm that the tissue core 850a removed by the coring cylinder 65 has been completely and cleanly removed from the aperture defined in the tissue wall 850. For example, in some embodiments, at least a portion of the handle 63 may comprise a transparent material such that the tissue core 850a received within the tissue core chamber 62 may be directly visible by a clinician and/or an endoscopic imaging device from a position substantially outside the handle 63. As shown in FIGS. 5F and 5G, after the coring device 2 (and the tissue core 850a retained in the handle 63 thereof) is retracted and removed from the inner tube 40, a clamp C may be applied to a proximal end of a graft portion that may be operably engaged with the inner tube 40 of the conduit device 1. In other embodiments, the inner tube 40 may comprise one or more ridges defined on an outer surface of the proximal end thereof that may be configured for receiving a deformable cap or other cover for temporarily and/or semi-permanently closing the aperture defined by the installed conduit device 1. As described herein, the conduit device 1 may be utilized as a portion of a two-part bypass system that may comprise another corresponding conduit device 1 installed in a tissue wall 850 defining a wall of the mammalian aorta, for example. The two corresponding conduit devices 1 may then be operably engaged with one another via a valve device so as to form an apicoaortic connection (AAC) in order to bypass, for example, a faulty valve or other mechanical defect present in a subject's cardiac anatomy.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A coring device comprising:
    a coring cylinder configured for advancing through a tissue wall to define an aperture in the tissue wall by removing a tissue core from the tissue wall, the coring cylinder defining a coring bore extending along a longitudinal axis of the coring device and configured for receiving the tissue core therein, wherein the tissue wall has a first surface and an opposed second surface;
    a retrieval device configured for piercing the tissue wall, the retrieval device comprising a corkscrew configured for retaining the tissue core; and
    an attaching device comprising a conical helix and configured for advancing along a helical path at least partially through the tissue wall such that at least a portion of the attaching device becomes disposed substantially between the first surface and opposed second surface of the tissue wall.

2. The coring device of claim 1, wherein the coring cylinder and the retrieval device are movable relative to one another in a direction of the longitudinal axis of the coring device.

3. The coring device of claim 1, wherein a longitudinal axis of the coring cylinder and a longitudinal axis of the retrieval device are coaxial with one another.

4. The coring device of claim 3, wherein the longitudinal axis of the coring cylinder and the longitudinal axis of the retrieval device are coaxial with the longitudinal axis of the coring device.

5. The coring device of claim 1, wherein the retrieval device is configured for piercing the tissue wall prior to removal of the tissue core from the tissue wall.

6. The coring device of claim 1, further comprising a handle engaged with the coring cylinder.

7. The coring device of claim 6, wherein the retrieval device and the handle are movable relative to one another in a direction of the longitudinal axis of the coring device.

8. The coring device of claim 6, further comprising a piercing rod engaged with the retrieval device, wherein the retrieval device and the piercing rod are movable relative to the coring cylinder and the handle in a direction of the longitudinal axis of the coring device.

9. The coring device of claim 8, wherein the piercing rod extends at least partially through the handle.

10. A method comprising:
 piercing a tissue wall with a retrieval device of a coring device, the retrieval device comprising a corkscrew, the corkscrew compressing at least a portion of the tissue wall inward;
 advancing a coring cylinder of the coring device through the tissue wall to define an aperture in the tissue wall by removing a tissue core from the tissue wall, the coring cylinder defining a coring bore extending along a longitudinal axis of the coring device and receiving the tissue core therein; and
 retaining the tissue core with the corkscrew wherein the corkscrew compresses the tissue against the coring device thereby forming a substantially fluid-tight seal between the tissue and the coring device.

11. The method of claim 10, wherein the tissue wall is pierced with the retrieval device prior to removing the tissue core from the tissue wall.

12. The method of claim 10, further comprising moving the coring cylinder and the retrieval device relative to one another in a direction of the longitudinal axis of the coring device.

13. The method of claim 12, wherein the coring cylinder and the retrieval device are moved relative to one another after piercing the tissue wall with the retrieval device.

14. The method of claim 12, wherein the coring cylinder and the retrieval device are moved relative to one another after advancing the coring cylinder through the tissue wall.

15. The method of claim 10, further comprising advancing an attaching device of a conduit device at least partially through the tissue wall prior to piercing the tissue wall with the retrieval device and prior to removing the tissue core from the tissue wall.

16. The method of claim 15, further comprising advancing the coring cylinder and the retrieval device at least partially through a central aperture of a ring of the conduit device, the ring surrounding at least a portion of the attaching device.

17. The method of claim 16, further comprising advancing an inner tube of the conduit device at least partially through the central aperture and at least partially through the aperture in the tissue wall.

18. A system comprising:
 a conduit device configured for attaching to a tissue wall, the conduit device comprising:
  an attaching device configured for advancing at least partially through the tissue wall;
  a ring surrounding at least a portion of the attaching device, the ring defining a central aperture extending therethrough; and
  a rigid inner tube configured for advancing at least partially through the central aperture, the inner tube defining a conduit aperture extending therethrough; and
 a coring device configured for defining an aperture in the tissue wall, the coring device comprising:
  a coring cylinder configured for advancing through the tissue wall to define the aperture in the tissue wall by removing a tissue core from the tissue wall, the coring cylinder defining a coring bore extending along a longitudinal axis of the coring device and configured for receiving the tissue core therein; and
  a retrieval device configured for piercing the tissue wall, the retrieval device comprising a corkscrew configured for retaining the tissue core and compressing the tissue against the outer surface of the inner tube.

19. The system of claim 18, wherein the coring cylinder and the retrieval device are configured for advancing at least partially through the central aperture.

20. The system of claim 18, wherein the coring cylinder and the retrieval device are configured for advancing at least partially through the conduit aperture.

\* \* \* \* \*